(12) United States Patent
Hunt

(10) Patent No.: US 10,129,491 B2
(45) Date of Patent: *Nov. 13, 2018

(54) ACTIVE REAL-TIME CHARACTERIZATION SYSTEM USING FIBER OPTIC-BASED TRANSMISSION MEDIA

(71) Applicant: The Boeing Company, Chicago, IL (US)

(72) Inventor: Jeffrey H. Hunt, Thousand Oaks, CA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/902,167

(22) Filed: Feb. 22, 2018

(65) Prior Publication Data

US 2018/0184016 A1    Jun. 28, 2018

Related U.S. Application Data

(63) Continuation of application No. 15/711,626, filed on Sep. 21, 2017, which is a continuation of application
(Continued)

(51) Int. Cl.
*H04N 5/33* (2006.01)
*G01N 21/88* (2006.01)
(Continued)

(52) U.S. Cl.
CPC ............... *H04N 5/332* (2013.01); *B64F 5/60* (2017.01); *G01N 21/8806* (2013.01);
(Continued)

(58) Field of Classification Search
CPC ........ H04N 5/332; H04N 5/2256; B64F 5/60; G01N 21/8806; G01N 21/95
See application file for complete search history.

(56) References Cited

U.S. PATENT DOCUMENTS 5,973,778 A * 10/1999 Hunt ...................... G01N 21/55
356/237.2
6,781,686 B2 * 8/2004 Hunt ...................... G01N 21/17
250/559.4

(Continued)

*Primary Examiner* — Anner N Holder
*Assistant Examiner* — Hesham K Abouzahra
(74) *Attorney, Agent, or Firm* — Toler Law Group, P.C.

(57) ABSTRACT

A system for providing active real-time characterization of an article under test is disclosed. An infrared light source, a first visible light source and a second visible light source each outputs and directs a beam of coherent light at a particular area on the article under test via respective optical fibers. A visible light camera and a visible light second harmonic generation camera, an infrared camera and an infrared second harmonic generation camera, a sum-frequency camera and a third-order camera are each configured to receive a respective return beam of light from the particular area on the article under test via respective optical fibers. A processor receives signals from the cameras and calculates in real time respective spectroscopic signals and compares each calculated signal with each other calculated signal and with a predetermined baseline signal to ensure that the article under test conforms to an expected value.

20 Claims, 4 Drawing Sheets

Related U.S. Application Data

No. 14/526,246, filed on Oct. 28, 2014, now Pat. No. 9,787,916.

(51) Int. Cl.

| | |
|---|---|
| *G01N 21/95* | (2006.01) |
| *H04N 5/225* | (2006.01) |
| *B64F 5/60* | (2017.01) |
| *G01N 21/84* | (2006.01) |

(52) U.S. Cl.
CPC ............ *G01N 21/95* (2013.01); *H04N 5/2256* (2013.01); *G01N 2021/8472* (2013.01); *G01N 2021/8845* (2013.01); *G01N 2201/0683* (2013.01)

(56) References Cited

U.S. PATENT DOCUMENTS

| | | |
|---|---|---|
| 6,788,405 B2 | 9/2004 | Hunt |
| 6,795,175 B2 | 9/2004 | Hunt |
| 6,798,502 B2 | 9/2004 | Hunt |
| 6,819,844 B2 * | 11/2004 | Hunt ...................... G01N 21/17 356/300 |
| 7,289,656 B2 * | 10/2007 | Engelbart .............. G01N 21/95 382/141 |
| 7,304,305 B2 | 12/2007 | Hunt |
| 7,757,558 B2 | 7/2010 | Bossi et al. |
| 7,983,469 B2 | 7/2011 | Engelbart et al. |
| 8,664,583 B2 | 3/2014 | Hunt et al. |
| 8,789,837 B2 | 7/2014 | Chang et al. |
| 9,151,941 B2 * | 10/2015 | Fresquet .................. G01B 9/04 |
| 2003/0231302 A1 * | 12/2003 | Hunt ...................... G01N 21/94 356/237.2 |
| 2003/0234360 A1 * | 12/2003 | Hunt .................. G01N 21/3563 250/339.06 |
| 2006/0039423 A1 * | 2/2006 | Tokuhisa ................ G02F 1/353 372/22 |
| 2013/0048841 A1 | 2/2013 | Hunt et al. |
| 2013/0050685 A1 | 2/2013 | Hunt et al. |
| 2013/0170509 A1 * | 7/2013 | Tokuhisa .............. H01S 3/0092 372/5 |
| 2016/0119557 A1 | 4/2016 | Hunt et al. |

* cited by examiner

ACTIVE REAL-TIME CHARACTERIZATION SYSTEM USING FIBER OPTIC-BASED TRANSMISSION MEDIA

RELATED APPLICATION

This patent arises from a continuation of U.S. patent application Ser. No. 15/711,626, filed Sep. 21, 2017, entitled "Active Real-Time Characterization System," which is hereby incorporated by reference in its entirety and which in turn is a continuation of U.S. patent application Ser. No. 14/526,246 (now U.S. Pat. No. 9,787,916), filed Oct. 28, 2014, entitled "Active Real-Time Characterization System," which is also hereby incorporated by reference in its entirety.

FIELD

This disclosure relates generally to an active real-time characterization system for use during composite overlay manufacturing that uses a fiber-optic-based transmission media.

BACKGROUND

In recent years, aircraft manufacturers have developed aircraft designs and aircraft fabrication methods that make greater use of carbon fiber composite materials and the like ("composite materials" or "CFCM"), such as graphite/epoxy, carbon fiber reinforced plastic ("CFRP") and graphite reinforced polymer ("GRP"). Composite materials are significantly lighter than traditional aircraft materials (e.g. aluminum, titanium, steel and alloys thereof), and can provide high strength with low weight, allowing lighter, more fuel efficient aircraft. In some newer aircraft, for example, the majority of the primary structure, including the fuselage and wing, is made of composite materials. One drawback in the growing use of carbon fiber composite materials is the lack of effective non-destructive evaluation type testing methodologies available for testing such materials during and after manufacture. In particular, there is a lack non-destructive evaluation type testing systems for providing real time characterization of composites during overlay manufacturing.

Accordingly, there is a need for a testing system which addresses the drawbacks identified above.

SUMMARY

In a first aspect, a system for providing active real-time characterization of an article under test is disclosed. An infrared light source outputs a beam of coherent infrared light. The infrared light source is configured to direct the beam of coherent infrared light at a particular area on the article under test via an associated optical fiber or bundle. A first visible light source outputs a first beam of coherent visible light. The first visible light source is configured to direct the first beam of coherent visible light at the same particular area on the article under test via an associated optical fiber or bundle. A visible light camera and a visible light second harmonic generation camera each configured to receive a first predetermined return beam of light from the particular area on the article under test via an associated optical fiber or bundle. An infrared camera and an infrared second harmonic generation camera are each configured to receive a second predetermined return beam of light from the particular area on the article under test via an associated optical fiber or bundle. A sum-frequency camera is configured to receive a third return beam of light from the particular area on the article under test via an associated optical fiber or bundle. A processor is coupled to receive signals from the visible light camera, the visible light second harmonic generation camera, the infrared camera, the infrared second harmonic generation camera and the sum-frequency camera. The processor is configured to calculate in real time a linear spectroscopic signal, a second harmonic generation spectroscopic signal and a sum-frequency spectroscopic signal. The processor is also configured to compare each calculated signal with each other calculated signal and with a predetermined baseline signal to ensure that the article under test conforms to an expected value.

In a further embodiment, a second visible light source may output a second beam of coherent visible light. The second visible light source may be configured to direct the second beam of coherent visible light at the same particular area on the article under test via an associated optical fiber or bundle. A third-order camera may be configured to receive a fourth return beam of light from the particular area on the article under test via an associated optical fiber or bundle. In this further embodiment, the processor may also be configured to calculate in real time a third-order spectroscopic signal and to compare the third-order spectroscopic signal with the other calculated signals and with a predetermined baseline signal to ensure that the article under test conforms to an expected value.

In a second aspect, a system for providing active real-time characterization of an article under test is disclosed. An infrared light source outputs a beam of coherent infrared light. The infrared light source is configured to direct the beam of coherent infrared light at a particular area on the article under test via an associated optical fiber or bundle. A first visible light source outputs a first beam of coherent visible light. The first visible light source is configured to direct the first beam of coherent visible light at the same particular area on the article under test via an associated optical fiber or bundle. A visible light camera and a visible light second harmonic generation camera are each configured to receive a first predetermined return beam of light from the particular area on the article under test via an associated optical fiber or bundle. An infrared camera and an infrared second harmonic generation camera are each configured to receive a second predetermined return beam of light from the particular area on the article under test via an associated optical fiber or bundle. A third-order camera is configured to receive a third return beam of light from the particular area on the article under test via an associated optical fiber or bundle. A processor is coupled to receive signals from the visible light camera, the visible light second harmonic generation camera, the infrared camera, the infrared second harmonic generation camera and the third-order camera. The processor is configured to calculate in real time a linear spectroscopic signal, a second harmonic generation spectroscopic signal and a third-order spectroscopic signal. The processor is also configured to compare each calculated signal with each other calculated signal and with a predetermined baseline signal to ensure that the article under test conforms to an expected value.

In a further embodiment, a second visible light source may output a second beam of coherent visible light. The second visible light source may be configured to direct the second beam of coherent visible light at the same particular area on the article under test via an associated optical fiber or bundle. A sum-frequency camera may be configured to receive a fourth return beam of light from the particular area on the article under test via an associated optical fiber or bundle. The processor may also be configured to calculate in real time a sum-frequency spectroscopic signal and to compare the sum-frequency spectroscopic signal with the other calculated signals and with a predetermined baseline signal to ensure that the article under test conforms to an expected value.

In either aspect, each of the sources may be coupled to an index control for setting the index of the respective output beam of light, a frequency control for setting a predetermined wavelength for the respective output beam of light, and a polarization control for setting a predetermined polarization for the respective output beam of light. Further, in either aspect, each of the cameras may be coupled to an index control for setting the index of the respective input beam of light, a frequency control for setting a predetermined wavelength for the respective input beam of light, and a polarization control for setting a predetermined polarization for the respective input beam of light. Finally, in ether aspect, the system may further include a beam splitter configured to split a return beam of light into two portions, a first portion directed to the visible light camera and a second portion directed to the visible light second harmonic generation camera.

In a still further aspect, a method for active real-time characterization of an article under test. Light from an infrared light source and a first visible light source is directed at an area on a surface of the article under test via associated respective optical fibers or bundles. Light from the infrared light source and first visible light source reflected from the surface of the article under test is directed to be received by a visible light camera, a visible light second harmonic generation camera, an infrared camera, an infrared second harmonic generation camera and a sum-frequency camera via associated respective optical fibers or bundles. Data is acquired from each of the cameras based on the received light. The data from each of the cameras is compared and contrasted, and correlations among the data are observed. Finally, the correlations among the data are analyzed and interpreted to determine if the composition of the article under test is within expected ranges. In a further embodiment, a second visible light source is also directed at the area on a surface of the article under test via an associated optical fiber or bundle, light from the first visible light source and the second visible light source reflected from the surface of the article under test is directed to be received by a third-order camera via an associated optical fiber or bundle, and the data from the third-order camera is acquired, analyzed and used to determine if the composition of the article under test is within expected ranges.

The features, functions, and advantages that have been discussed can be achieved independently in various embodiments or may be combined in yet other embodiments, further details of which can be seen with reference to the following description and drawings.

BRIEF DESCRIPTION OF THE DRAWINGS

The following detailed description, given by way of example and not intended to limit the present disclosure solely thereto, will best be understood in conjunction with the accompanying drawings in which.

DETAILED DESCRIPTION

In the present disclosure, like reference numbers refer to like elements throughout the drawings, which illustrate various exemplary embodiments of the present disclosure.

Figure 1:
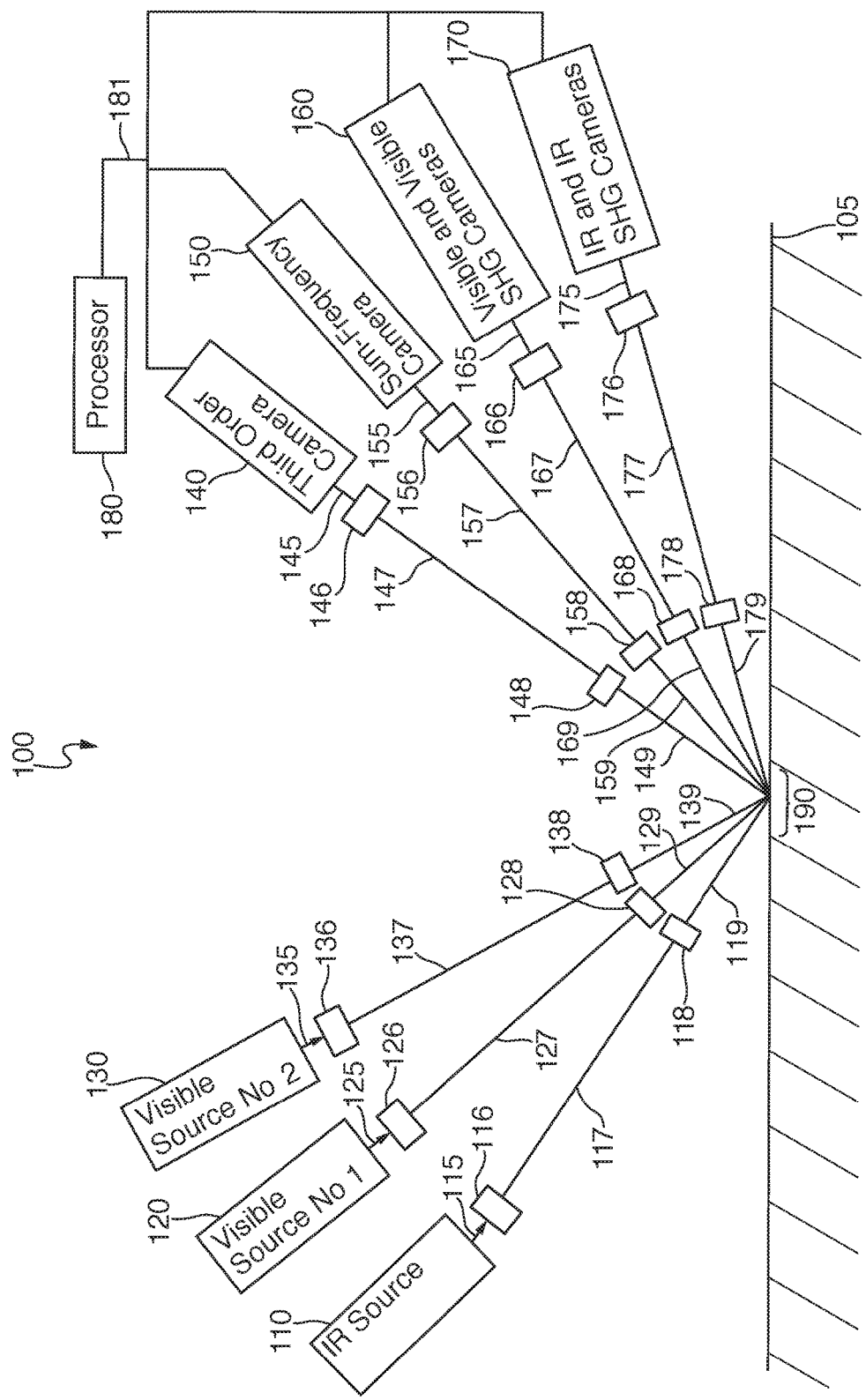
FIG. 1 is a block diagram of one embodiment of an active real-time characterization system for use during composite overlay manufacturing according to an aspect of the present disclosure.

Referring now to FIG. 1, the active real-time characterization system 100 of the present disclosure includes an infrared (IR) light source 110, a first visible light source 120 and a second visible light source 130. Each of the light sources 110, 120, 130 is positioned to direct a beam 119, 129, 139 of coherent light at an area 190 on a surface of an article under test 105, e.g., a part constructed from carbon-fiber composites, via an associated optical fiber or bundle 117, 127, 137. In particular, IR source 110 is positioned to direct a coherent beam of light 119 at area 190, first visible light source 120 is positioned to direct a coherent beam of light 129 at area 190, and send visible light source 130 is positioned to direct a coherent beam of light 139 at area 190. Each light source 110, 120 130 consists of a laser of the appropriate type (visible or IR light) that outputs respective beams 115, 125, 135 into a respective input optics module 116, 126, 136. Each input optics module 116, 126, 136 is in turn coupled to a respective associated optical fiber or bundle 117, 127, 137. The lasers forming light sources 110, 120, 130 are each preferably a solid state laser or a diode laser and may be, for example, a diode laser, a continuous-wave diode laser, a solid state laser, a continuous-wave solid state laser, a flash-lamp pumped solid state laser, or a diode pumped solid state laser. The input optics modules 116, 126, 136 each consists of an input polarizer, an input wavelength discriminator, an input spatial filter and an input propagation optics. The input polarizer is, for example, a Brewster angle polarizer, a thin film polarizer, a Glan-air or Glan-Thompson polarizer or other crystal polarizer. The wavelength discriminator is, for example, a color filter, a dielectric film, a holographic transmission filter, or a grating. The input propagation optics is formed of one or more refractive or reflective optics which, when used in combination, control the divergence or convergence of the beam as it propagates towards the first input optical fiber. The input optics modules 116, 126, 136 are each optimized for the wavelength of the associated optical source 110, 120, 130. Respective coupling optics modules 118, 128, 138 are coupled to an output of an associated optical fiber or bundle 117, 127, 137 to direct the beam to area 190. IR light source 110 is configured to output light at a fixed, predetermined IR wavelength, while first visible light source 120 is configured to output light at a first fixed, predetermined visible wavelength and second visible light source 130 is configured to output light at a second fixed, predetermined visible wavelength, different from the first fixed, predetermined visible wavelength.

System 100 in FIG. 1 also includes a number of cameras 140, 150 and camera pairs 160, 170 for detecting light reflected from the surface of article under test 105 via associated optical fibers or bundles 147, 157, 167, 177. A Raman (third-order) camera 140 receives a light beam 145.

Sum-frequency camera 150 receives a light beam 155. Paired visible and visible second harmonic generation (SHG) cameras 160 each receive a light beam 165. Finally, paired IR and IR SHG cameras 170 receive a light beam 175. Each of the optical fibers or bundles 147, 157, 167, 177 is coupled to an associated input optics module 148, 158, 168, 178 for receiving, respectively, return light beams 149, 159, 169, 179. In addition, each of the optical fibers or bundles 147, 157, 167, 177 is coupled to respective output optics modules 146, 156, 166, 176 for directing the associated light beams 145, 155, 165, 175 to cameras 140, 150 and camera pairs 160, 170.

Figure 2:
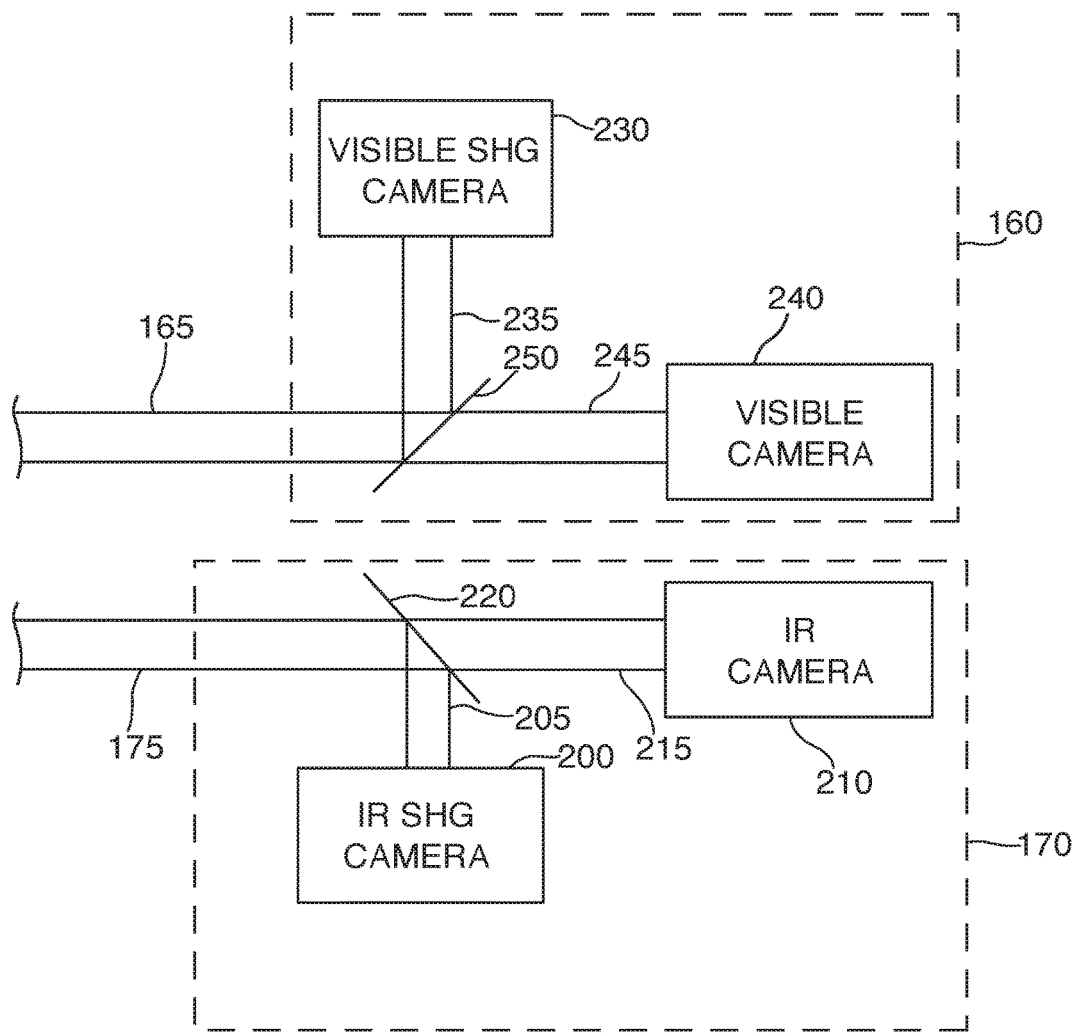
FIG. 2 is a block diagram showing the composition of the infrared light and visible light camera systems according to an aspect of the present disclosure.

Referring now to FIG. 2, the paired visible light and visible light second harmonic generation (SHG) cameras 160 include a visible light SHG camera 230 and a visible light camera 240 which are positioned to each receive light beam 165 via a beam splitter 250. In particular, beam splitter 250 is positioned to split light beam 165 into a first portion 235 that is provided to visible light SHG camera 230 and a second portion 245 that is provided to visible light camera 240. Similarly, the paired IR and IR second harmonic generation (SHG) cameras 170 include an IR SHG camera 200 and an IR camera 210 which are positioned to each receive light beam 175 via a beam splitter 220. In particular, beam splitter 220 is positioned to split light beam 175 into a first portion 205 that is provided to IR SHG camera 200 and a second portion 215 that is provided to IR camera 210. Each of the cameras 140, 150, 200, 210, 230 and 240 produces an output signal that is communicated in a conventional manner to a processor 180 via a link 181 for processing as discussed below. The reflected light beams 145, 155, 165 and 175 are at a particular angle with respect to the surface of device under test 105 based on the mounting position of coupling optics modules 118, 128, 138 and input optics modules 148, 158, 168, 178 with respect to the surface of device under test 105. Each of the coupling optics modules 118, 128, 138, 148, 158, 168, 178 must be mounted to fixed optical mounts to ensure that the respective light beams are directed at or received from the surface at the appropriate angle. The cameras 140, 150, 200, 210, 230 and 240 are thus configured to receive the respective reflected light beams via the optical fibers or bundles 147, 157, 167, 177. Each camera 140, 150, 200, 210, 230, 240 is a conventional detector as defined below with respect to FIG. 4.

As one of ordinary skill in the art will readily recognize, light sources 110, 120, 130 and cameras 140, 150, 200, 210, 230 and 240 may be fixed in place and article under test 105 may be moved so that the area 190 of the light beams 115, 125, 135 moves over the entire surface of article under test 105. In another embodiment, light sources 110, 120, 130 and cameras 140, 150, 200, 210, 230 and 240 may be mounted on a fixture that moves along the surface of article under test 105. In yet another embodiment, light sources 110, 120, 130 may be arranged to raster the respective output light beams 115, 125, 135 across the surface of the article under test 105, and the detectors 140, 150, 200, 210, 230 and 240 arranged to move proportionally to receive the respective associated return light beams 145, 155, 165, 175.

Figure 3:
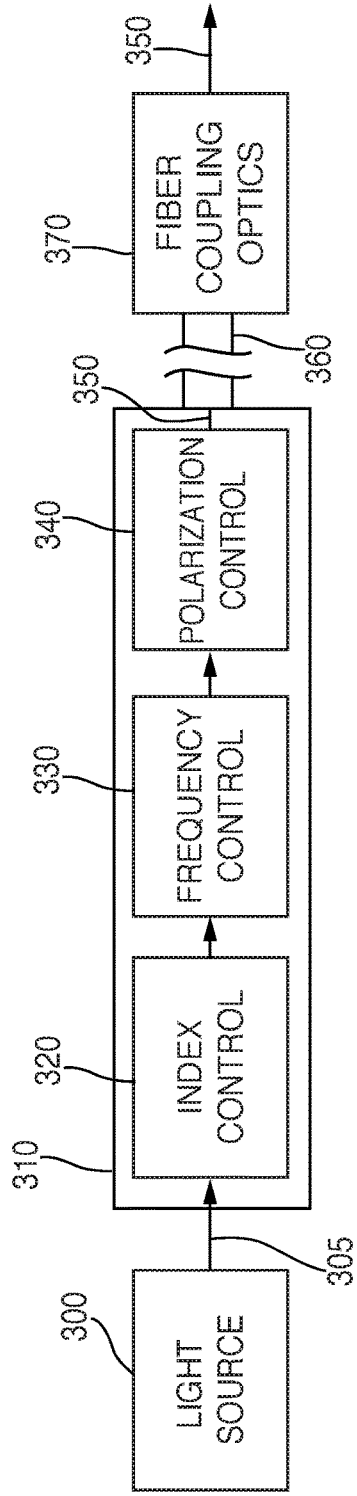
FIG. 3 is a block diagram showing the composition of the light sources according to an aspect of the present disclosure.

Referring now to FIG. 3, each of the light sources 110, 120, 130 is similarly coupled to a respective associated optical fiber or bundle 117, 127, 137, as shown by representative light source 300 coupled to representative optical fiber or bundle 360, but each may be configured for a different index, frequency and/or polarization as appropriate. Light source 300 outputs a light beam 305 to input optics module 310. Input optics module 210 includes an index control 320, a frequency control 330 and a polarization control 340 for outputting a light beam 350 onto optical fiber or bundle 360. Light source 300 is preferably a narrow frequency bandwidth visible pulse laser and, may be, for example a pulsed diode laser, a continuous wave diode laser or a pulsed solid state laser or a continuous wave solid state laser. Index control 320 provides index compensation. Frequency control 330 can be accomplished in simple cases by frequency dependent color filters or notch filters and in more elaborate by a spectrophotometer that is typically composed of a diffraction grating which operates at a frequency or bandwidth of interest. The key point for the frequency control 330 is to ensure that only light in beam 350 is directed at the surface 105 and that stray light produced by light emitter 310 is removed, and as one of ordinary skill in the art will readily recognize, other frequency selective elements may also be used. Polarization control 340 consists of two separate optical elements, a polarizer which only passes light of one polarization and a polarization modifying element—typically a halfway plate or a quarter wave plate. A halfway plate is used to rotate the polarization to the desired orientation. A quarter wave plate is used to change the polarization from linear to circular or from circular to linear as needed. As shown, the polarizer is the last element before light beam 350 leaves the source and enters a first end of optical fiber or bundle 360. Fiber coupling optics 370 at a second end of optical fiber or bundle 360 direct the light beam 350 in a particular direction, i.e., towards a particular point on the surface of the article under test 105. In this manner, each light source 110, 120, 130 is set, based on the selection of light source 300, index control 320, frequency control 330 and polarization control 340 in each, to provide a respective coherent beam of light 119, 129, 139 at a common point on the surface of article under test 105 via the respective associated coupling optics modules 118, 128, 138.

Figure 4:
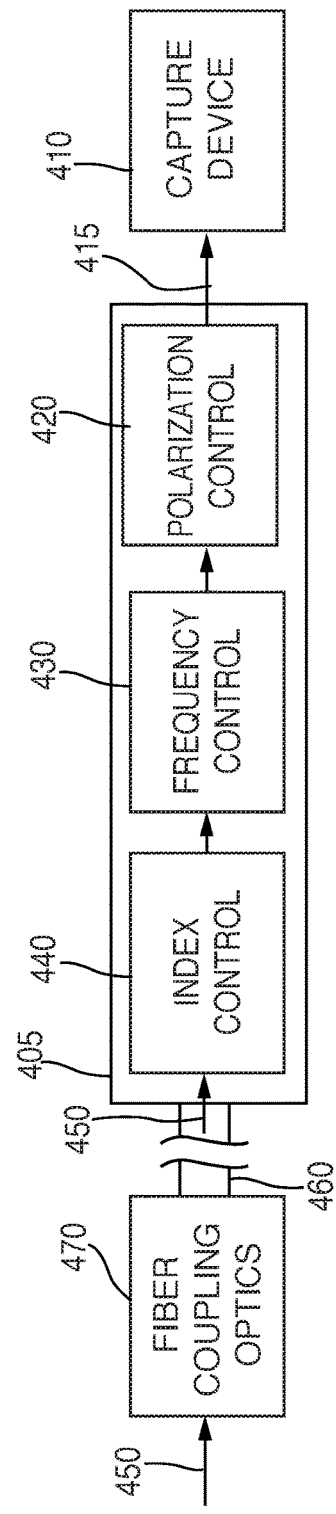
FIG. 4 is a block diagram showing the composition of the cameras according to an aspect of the present disclosure.

Each of the cameras 140, 150 and camera pairs 160, 170 is similarly coupled to a respective associated optical fiber or bundle 147, 157, 167, 177. Referring now to FIG. 4, a return light signal 450 (separately corresponding to each of the return light signals 149, 159, 169, 179 shown in FIG. 1) is first provided to fiber coupling optics 470 which directs the light beam 450 into a first end of an optical fiber or bundle 460. The light beam 450 exits at a second end of the optical fiber or bundle 460 and enters an output optics module 405. The output optics module 405 includes an index control 440, a frequency control 430 and a polarization control 420. Light beam 415 exits output optics module 420 (light beam 415 corresponds to light beam 450 after passing through index control 440, frequency control 430 and polarization control 420) and is provided to a representative capture device 410 for signal capture. Exemplary capture devices 410 include, without limitation, cameras, CCD devices, imaging arrays, photometers, and like devices. Frequency control 430 and index control 440 operate on light beam 450 in a similar manner as index control 320 and frequency control 330 operate on light beam 350 as discussed above. Preferably, polarization control 420 consists of a half wave plate and quarter wave combination, followed by a polarizer.

In operation, system 100 shown in FIG. 1 provides a combination of linear infrared spectroscopy, second order surface frequency mixing spectroscopy, and third-order non-linear optics (e.g., Raman spectroscopy) spectroscopy. System 100 provides a number of ways of performing species identification and allows the cross correlation between the three types of spectroscopies in order to avoid false negative spectral features.

In particular, visible light source 120 and IR light source 110 are configured and positioned to provide light signals which allow the processor 180 to generate simultaneous linear (same frequency) and non-linear (second harmonic generation) real time spectroscopic signals, in conjunction with paired visible light and visible light second harmonic generation (SHG) cameras 160 and paired IR and IR SHG cameras 170. As one of ordinary skill in the art will readily recognize, paired visible light and visible light second harmonic generation (SHG) cameras 160 and paired IR and IR SHG cameras 170 are positioned at a particular predetermined angle to receive the appropriate respective return light signals 165, 175 from surface 105.

Further, visible light source 120 and IR light source 110 are also configured and positioned to provide light signals which allow the processor 180 to generate a sum-frequency ($\omega_{IR}+\omega_{VISIBLE}$) real-time spectroscopic signal, in conjunction with sum-frequency camera 150. As one of ordinary skill in the art will readily recognize, sum-frequency camera 140 is positioned at a particular predetermined angle to receive the appropriate return light signals 155 from surface 105.

Finally, visible light source 120 and visible light source 130 are configured and positioned to provide light signals which allow the processor 180 to generate a third-order ($2\omega_{VIS1}-\omega_{VIS2}$) (e.g., Raman) real-time spectroscopic signal, in conjunction with Raman (third-order) camera 140. As one of ordinary skill in the art will readily recognize, Raman (third-order) camera 140 is positioned at a particular predetermined angle to receive the appropriate return light signals 145 from surface 105.

The processor 180 is coupled to receive signals from each of cameras 140, 150, 200, 210, 230 and 240 and is configured to calculate in real time a linear spectroscopic signal, a second harmonic generation spectroscopic signal, a sum-frequency spectroscopic signal and a third-order spectroscopic signal. The processor 180 is also configured to compare each calculated signal with each other calculated signal and with a predetermined baseline signal to ensure that the article under test conforms to an expected value. When the processor 180 determines that the calculated signals indicate that the article under test does not conform to the expected value, processor 180 provides a fault signal which may be used to halt formation of the part under test 105 for either repair thereof or so that part under test 105 may be immediately discarded.

Figure 5:
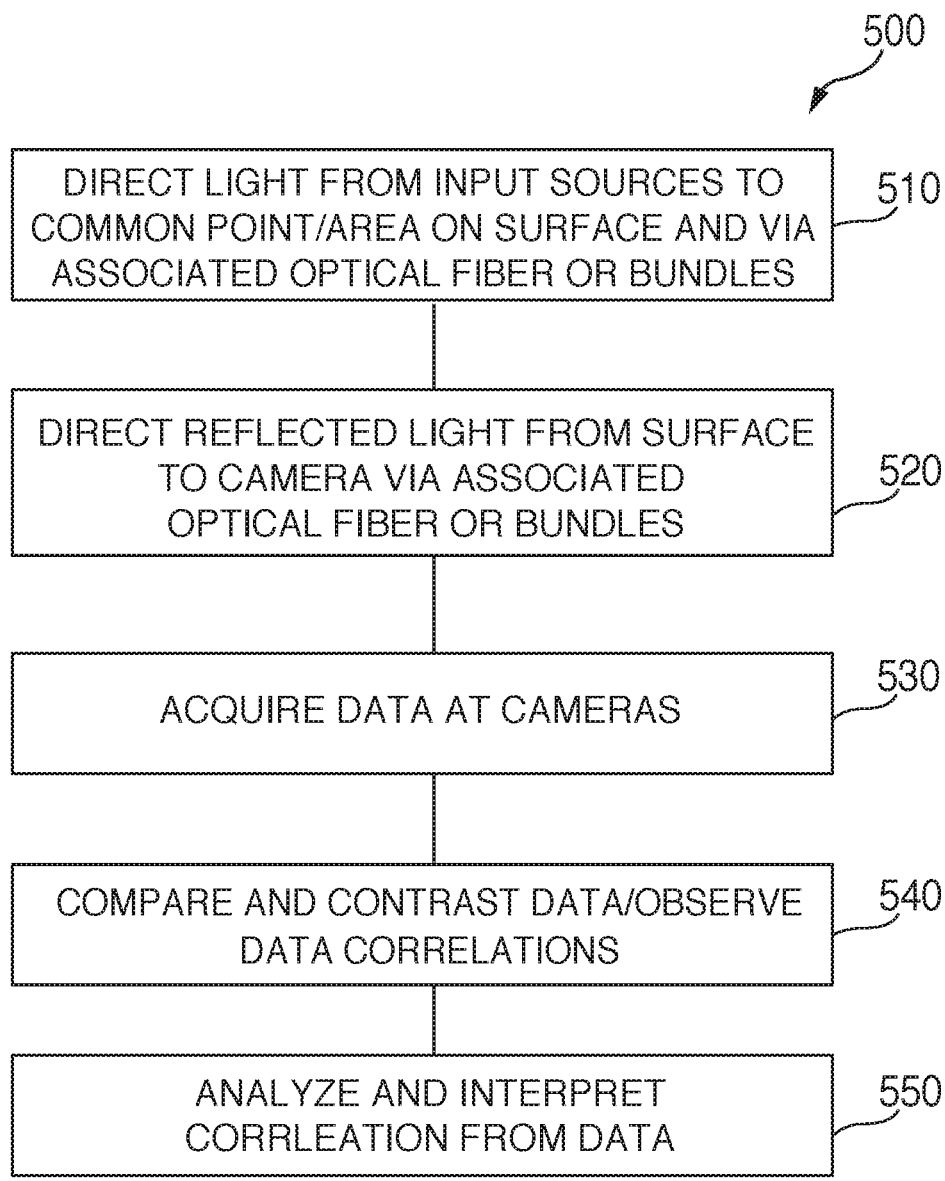
FIG. 5 is a flow chart of a method for operating the active real-time characterization system of the present disclosure.

Referring now to FIG. 5, a flow chart 500 of a method for operating the active real-time characterization system of the present disclosure is shown. In step 510, light from the each of the input light sources is directed at common point or area on the surface of the article under test via associated optical fibers or bundles. Next, at step 520, light reflected from the input sources is directed to each of the cameras via associated optical fibers or bundles. As evident from the discussion above, each of the third-order camera 140, the sum-frequency camera 150, the visible light and visible light SHG cameras and the IR and IR SHG cameras have separate associated optical fibers or bundles. Further, at step 530, data is acquired at each of the cameras/detectors. After this, at step 540, the acquired data is compared and contrasted, and correlations among the data are observed. Finally, at step 550, the correlations among the data are analyzed and interpreted to determine whether or not the composition of the article under test falls within expected ranges.

As one of ordinary skill in the art will readily recognize, the active-real time characterization system 100 of the present disclosure may be applied to testing for composition of the article under test, for identifying contamination on the surface of the article under test or for a combination of both material composition and contamination identification. In addition, the active real-time characterization system 100 of the present disclosure may be used to test graphite fiber-based materials, polymer/plastic materials, glass fiber reinforcement-based materials such as fiberglass and glass laminate aluminum reinforced epoxy ("GLARE"), resins, plastics or polymers without reinforcement fibers, metals, and ceramics including glass materials.

By providing a combination of linear, non-linear, sum-frequency and third-order real time spectroscopic signals, the present system provides the ability to more accurately monitor the chemistry of composite parts during formation by avoiding false negative spectral features. This system can allow, in some cases, defects to be repaired and thus prevent the loss of the composite part. In other cases, this system can ensure that production is halted as soon as a defect is identified, and thus preventing further costly work from being performed on a composite part destined to be discarded.

In further embodiments, the data generated by the active-real time characterization system 100 of the present disclosure may be combined for analysis with data separately generated by way of UV-VIS-NIR spectroscopy, IR spectroscopy, microwave spectroscopy, THz spectroscopy, ultrasonic NDE/NDI, Raman spectroscopy, Brillouin spectroscopy and/or ellipsometry.

Although the present disclosure has been particularly shown and described with reference to the preferred embodiments and various aspects thereof, it will be appreciated by those of ordinary skill in the art that various changes and modifications may be made without departing from the spirit and scope of the disclosure. It is intended that the appended claims be interpreted as including the embodiments described herein, the alternatives mentioned above, and all equivalents thereto.

What is claimed is:

1. A system for providing active real-time characterization of an article under test, comprising:
   an infrared light source for outputting a beam of coherent infrared light, the infrared light source configured to direct the beam of coherent infrared light at a particular area on the article under test via an associated optical fiber or bundle;
   a first visible light source for outputting a first beam of coherent visible light, the first visible light source configured to direct the first beam of coherent visible light at the same particular area on the article under test via an associated optical fiber or bundle;
   a visible light camera and a visible light second harmonic generation camera, the visible light camera and visible light second harmonic generation camera each configured to receive a first predetermined return beam of light from the particular area on the article under test via an associated optical fiber or bundle;
   an infrared camera and an infrared second harmonic generation camera, the infrared camera and infrared second harmonic generation camera each configured to receive a second predetermined return beam of light from the particular area on the article under test via an associated optical fiber or bundle;
   a sum-frequency camera configured to receive a third return beam of light from the particular area on the article under test via an associated optical fiber or bundle; and a processor coupled to receive signals from the visible light camera, the visible light second harmonic generation camera, the infrared camera, the infrared second harmonic generation camera and the sum-frequency camera, the processor configured to calculate in real time a linear spectroscopic signal, a second harmonic generation spectroscopic signal and a sum-frequency spectroscopic signal, the processor also configured to compare each calculated signal with each other calculated signal and with a predetermined baseline signal to ensure that the article under test conforms to an expected value.

2. The system of claim 1, further comprising:
a second visible light source for outputting a second beam of coherent visible light, the second visible light source configured to direct the second beam of coherent visible light at the same particular area on the article under test via an associated optical fiber or bundle;
a third-order camera configured to receive a fourth return beam of light from the particular area on the article under test via an associated optical fiber or bundle; and
wherein the processor is also configured to calculate in real time a third-order spectroscopic signal and to compare the third-order spectroscopic signal with the other calculated signals and with a predetermined baseline signal to ensure that the article under test conforms to an expected value.

3. The system of claim 1, wherein each of the sources is coupled to an index control for controlling the index of the respective output beam of light.

4. The system of claim 1, wherein each of the sources is coupled to a frequency control for setting a predetermined wavelength for the respective output beam of light.

5. The system of claim 1, wherein each of the sources is coupled to a polarization control for setting a predetermined polarization for the respective output beam of light.

6. The system of claim 1, wherein each of the cameras is coupled to an index control for controlling the index of the respective input beam of light.

7. The system of claim 1, wherein each of the cameras is coupled to a frequency control for setting a predetermined wavelength for the respective input beam of light.

8. The system of claim 1, wherein each of the cameras is coupled to a polarization control for setting a predetermined polarization for the respective input beam of light.

9. The system of claim 1, further comprising a beam splitter configured to split a return beam of light into two portions, a first portion directed to the visible light camera and a second portion directed to the visible light second harmonic generation camera.

10. A system for providing active real-time characterization of an article under test, comprising:
an infrared light source for outputting a beam of coherent infrared light, the infrared light source configured to direct the beam of coherent infrared light at a particular area on the article under test via an associated optical fiber or bundle;
a first visible light source for outputting a first beam of coherent visible light, the first visible light source configured to direct the first beam of coherent visible light at the same particular area on the article under test via an associated optical fiber or bundle;
a visible light camera and a visible light second harmonic generation camera, the visible light camera and visible light second harmonic generation camera each configured to receive a first predetermined return beam of light from the particular area on the article under test via an associated optical fiber or bundle;
an infrared camera and an infrared second harmonic generation camera, the infrared camera and infrared second harmonic generation camera each configured to receive a second predetermined return beam of light from the particular area on the article under test via an associated optical fiber or bundle;
a third-order camera configured to receive a third return beam of light from the particular area on the article under test via an associated optical fiber or bundle; and
a processor coupled to receive signals from the visible light camera, the visible light second harmonic generation camera, the infrared camera, the infrared second harmonic generation camera and the third-order camera, the processor configured to calculate in real time a linear spectroscopic signal, a second harmonic generation spectroscopic signal and a third-order spectroscopic signal, the processor also configured to compare each calculated signal with each other calculated signal and with a predetermined baseline signal to ensure that the article under test conforms to an expected value.

11. The system of claim 10, further comprising:
a second visible light source for outputting a second beam of coherent visible light, the second visible light source configured to direct the second beam of coherent visible light at the same particular area on the article under test via an associated optical fiber or bundle;
a sum-frequency camera configured to receive a fourth return beam of light from the particular area on the article under test via an associated optical fiber or bundle; and
wherein the processor is also configured to calculate in real time a sum-frequency spectroscopic signal and to compare the sum-frequency spectroscopic signal with the other calculated signals and with a predetermined baseline signal to ensure that the article under test conforms to an expected value.

12. The system of claim 10, wherein each of the sources is coupled to an index control for controlling the index of the respective output beam of light.

13. The system of claim 10, wherein each of the sources is coupled to a frequency control for setting a predetermined wavelength for the respective output beam of light.

14. The system of claim 10, wherein each of the sources is coupled to a polarization control for setting a predetermined polarization for the respective output beam of light.

15. The system of claim 10, wherein each of the cameras is coupled to an index control for controlling the index of the respective input beam of light.

16. The system of claim 10, wherein each of the cameras is coupled to a frequency control for setting a predetermined wavelength for the respective input beam of light.

17. The system of claim 10, wherein each of the cameras is coupled to a polarization control for setting a predetermined polarization for the respective input beam of light.

18. The system of claim 10, further comprising a beam splitter configured to split a return beam of light into two portions, a first portion directed to the visible light camera and a second portion directed to the visible light second harmonic generation camera.

19. A method for active real-time characterization of an article under test, comprising the steps of:
directing light from an infrared light source and a first visible light source at an area on a surface of the article under test via associated respective optical fibers or bundles;

directing light from the infrared light source and first visible light source reflected from the surface of the article under test to be received by a visible light camera, a visible light second harmonic generation camera, an infrared camera, an infrared second harmonic generation camera and a sum-frequency camera via associated respective optical fibers or bundles;

acquiring data from each of the cameras based on the received light;

comparing and contrasting the data from each of the cameras and observing correlations among the data; and analyzing and interpreting the correlations among the data to determine if the composition of the article under test is within expected ranges.

20. The method of claim 19, further comprising the steps of:

directing light from a second visible light source at the area on the surface of the article under test via an associated optical fiber or bundle;

directing light from the first visible light source and the second visible light source reflected from the surface of the article under test to be received by a third-order camera via an associated optical fiber or bundle;

acquiring data from the third-order camera; and using the data from the third-order camera in the comparing and contrasting steps and analyzing and interpreting steps.

* * * * *